(12) United States Patent
Manges

(10) Patent No.: US 9,763,037 B2
(45) Date of Patent: *Sep. 12, 2017

(54) NETWORK ARCHITECTURE FOR SYNCHRONIZED DISPLAY

(71) Applicant: MEDAPPIT LLC, Cincinnati, OH (US)

(72) Inventor: Barbara J. Manges, Cincinnati, OH (US)

(73) Assignee: MEDAPPIT LLC, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/182,321

(22) Filed: Jun. 14, 2016

(65) Prior Publication Data

US 2017/0064498 A1 Mar. 2, 2017

Related U.S. Application Data

(60) Continuation-in-part of application No. 14/834,108, filed on Aug. 24, 2015, now Pat. No. 9,369,839, (Continued)

(51) Int. Cl.

| G06F 15/173 | (2006.01) |
|---|---|
| G06F 15/177 | (2006.01) |
| H04W 4/02 | (2009.01) |
| H04L 29/08 | (2006.01) |
| H04W 76/02 | (2009.01) |

(Continued)

(52) U.S. Cl.
CPC ............ *H04W 4/02* (2013.01); *G06F 3/1454* (2013.01); *H04L 67/12* (2013.01); *H04L 67/18* (2013.01); *H04N 1/00* (2013.01); *H04W 4/008* (2013.01); *H04W 4/028* (2013.01); *H04W 4/046* (2013.01); *H04W 12/06* (2013.01); *H04W 64/00* (2013.01); *H04W 76/023* (2013.01); *H04W 84/005* (2013.01); *B64C 39/024* (2013.01); *B64C 2201/122* (2013.01); *G06F 19/3406* (2013.01); *H04W 84/10* (2013.01); *H04W 84/18* (2013.01)

(58) Field of Classification Search
USPC ....... 709/204, 223, 228, 203, 206, 217, 219, 709/220, 224, 226, 232, 238; 701/124, 701/409; 725/60; 455/456.1
See application file for complete search history.

(56) References Cited

U.S. PATENT DOCUMENTS

| 8,117,341 B2 * | 2/2012 | Matz ...................... H04W 4/02 709/228 |
|---|---|---|
| 8,135,505 B2 * | 3/2012 | Vengroff ............... G06Q 30/02 701/24 |

(Continued)

*Primary Examiner* — Quang N Nguyen
(74) *Attorney, Agent, or Firm* — Jenei LLC; Stephen Jenei

(57) ABSTRACT

Systems and methods are provided that couple one or more devices to one or more user interfaces and to one or more servers via network connections allowing a human operator to provide tailored content to an autonomous or semi-autonomous robotic agent that is responsive to human interpretable commands. Various devices can be identified on a network and location data regarding each of the mobile devices can be delivered to the servers. Data can be displayed on a user interface that is a presentation screen based on mobile devices in its proximity, for example.

3 Claims, 9 Drawing Sheets

Related U.S. Application Data which is a continuation-in-part of application No. 14/584,123, filed on Dec. 29, 2014, now Pat. No. 9,119,031, which is a division of application No. 13/475,146, filed on May 18, 2012, now Pat. No. 8,924,594.

(60) Provisional application No. 61/487,380, filed on May 18, 2011.

(51) Int. Cl.
*H04W 4/00* (2009.01)
*G06F 3/14* (2006.01)
*H04N 1/00* (2006.01)
*H04W 4/04* (2009.01)
*H04W 12/06* (2009.01)
*H04W 64/00* (2009.01)
*H04W 84/00* (2009.01)
*G06F 19/00* (2011.01)
*H04W 84/10* (2009.01)
*H04W 84/18* (2009.01)
*B64C 39/02* (2006.01)

(56) References Cited

U.S. PATENT DOCUMENTS

| | | | |
|---|---|---|---|
| 8,744,352 B2* | 6/2014 | Pochop, Jr. | H04W 16/18 709/223 |
| 8,928,483 B2* | 1/2015 | Nasir | G07C 1/10 455/456.1 |
| 2002/0049975 A1* | 4/2002 | Thomas | G06Q 50/34 725/60 |
| 2012/0136565 A1* | 5/2012 | Kennedy | G01C 21/367 701/409 |
| 2013/0040657 A1* | 2/2013 | Jackson | G06F 21/84 455/456.1 |
| 2014/0012918 A1* | 1/2014 | Chin | G06Q 50/01 709/204 |
| 2015/0154851 A1* | 6/2015 | Vincent | G06F 17/30241 340/539.13 |

* cited by examiner

NETWORK ARCHITECTURE FOR SYNCHRONIZED DISPLAY

CROSS-REFERENCE TO RELATED APPLICATION

This application is a continuation-in-part of U.S. nonprovisional patent application Ser. No. 14/834,108, filed on Aug. 24, 2015 (issuing as U.S. Pat. No. 9,369,839 on Jun. 14, 2016), which in turn is continuation-in-part of U.S. nonprovisional patent application Ser. No. 14/584,123, filed on Dec. 29, 2014 (issued as U.S. Pat. No. 9,119,031), which in turn is a divisional of U.S. nonprovisional patent application Ser. No. 13/475,146, filed on May 18, 2012 (issued as U.S. Pat. No. 8,924,594), which claims the benefit of U.S. provisional patent application Ser. No. 61/487,380, filed on May 18, 2011, entitled "Network Architecture for Synchronized Display," the disclosures of which are hereby incorporated by reference herein in their entirety.

BACKGROUND

Mobile devices (e.g., handheld computing devices, personal digital assistants, wireless phones, portable game devices, tablets, netbooks, and so on) have become an integral part of everyday life. Accustomed to the instant gratification that mobile devices provide, consumers demand results from service providers substantially in real-time. However, many industries lag behind when it comes to having service providers present results visually in substantially real-time to consumers during in-person meetings, teleconferences and virtual encounters. For example, consumers of financial, healthcare and educational services demand visual results in substantially real-time during in-person meetings. For example, mobile devices may have a relatively limited amount of display area when compared to a conventional desktop computer, such as a PC.

Furthermore, the retail consumer and industry demand for mobile devices is rising, while the demand for traditional desktop computing devices (e.g., PCs) is decreasing. For example, the healthcare industry purchased 8.8 billion mobile devices in 2010, which was a 7% increase over the previous year. Industries have found that using mobile devices in the workplace reduces costs and increases productivity.

BRIEF DESCRIPTION OF THE DRAWINGS

While the specification concludes with claims particularly pointing out and distinctly claiming the subject matter, it is believed that the embodiments will be better understood from the following description in conjunction with the accompanying figures, in which:

DETAILED DESCRIPTION

Figure 1:
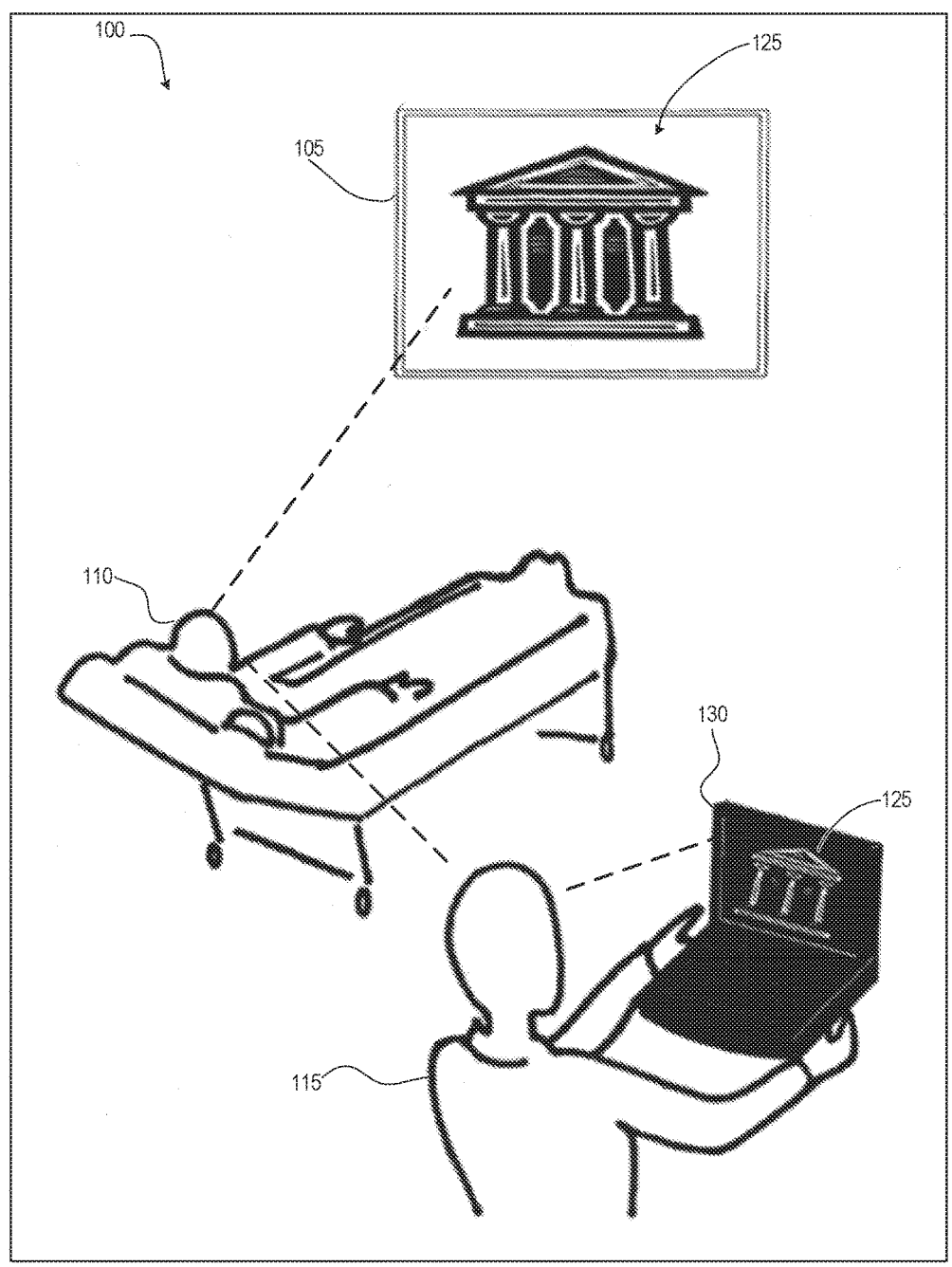
FIG. 1 illustrates an operating environment in which various principles described herein can be employed in accordance with one or more embodiments.

The present innovation has applications to a rapidly expanding technology associated with so-called soft robotics or compliant robotics. Humanoid robots are being developed and refined and made more economical. As used herein, humanoid robots can in some instances imitate the form of a human or a part of a human. A humanoid robot can also be articulated in a very different manner but replace a human operator in performing one or more tasks. The humanoid robotic system can be connected to the network by any and all available means such as wireless, ad-hoc networking, mesh networking, 4G LTE, LAN/WAN, etc. The humanoid robotic systems, much like the ones created by a Google owned (for sale) company Boston Dynamics, are capable of receiving commands from human operators and can complete a variety of tasks. Soon these systems will work independently of human operators and will only receive commands from the network to which they are attached in this case the software and technology behind it. In a warehouse setting these systems will be able to operate machinery, stack and rack boxes, move equipment, all while connected to the network through the connections previously mentioned. These systems will not only be used in this environment but, by the year 2025 a robotic systems of some form will be in every home and it may as well be one that is connected to this network.

Humanoid robots are becoming available that have articulated arms that have a resilient exterior and manually back drivable joints. Such devices can seamlessly work in place of a human and among humans. For example, an order fulfillment center in a distribution center can convey totes or containers of products to a picking station where traditionally a human operator performed an each picking procedure to place a requested number of items into an order tote or container. Augmenting such an enterprise in a gradual procedure can entail replacing certain human operators with an each picking robot. Since the each picking robot can be designed with compliant arms, a human operator can safely work in proximity to the each picking robot. The mass and momentum of the compliant arms in combination with their soft exterior and back drivable joints prevent serious injury to a human operator.

Soft robotics can also include making such robots economical to use in a range of activities currently performed by a human operator. These systems can have a basic motor function capability that can be taught in a human-like manner to perform a repetitive procedure. A human can manually move the arm of the robot to perform a task and by so doing teach the robot how to do a task. Graphical user interfaces can also facilitate basic instructions to the robot without requiring the human operator to have sophisticated expertise in robotic programming.

Other measures are being made to make humanoid robots more economical and acceptable for user amongst human operators. For example, requiring less precision in movement can be compensated by having the humanoid robot be able to sense the resulting position and to compensate for any error. Requiring less predictable movement can greatly reduce the cost of the moving parts of the humanoid robot. Another advancement continues in speech recognition and interpretation. Yet another area of advancement is improved machine vision, recognizing shapes in a less than routine environment.

Consequently, humanoid robots are likely to soon proliferate that are somewhat or entirely autonomous and that are instructed in a human-like manner. Such humanoid robots can take over the mundane tasks of household cleaning. Such humanoid robots can be directed to enter into areas hazardous for human operators, such as in law enforcement or military engagement areas or environmentally hazardous situations.

In some situations or for other humanoid robots, command and control can be largely dependent upon network control. Actions of multiple of humanoid robots in an orchestrated manner may be required to accomplish a project. Simpler and more economical humanoid robots may be incapable of sophisticated decision making, which is performed in centralized fashion. The command and control system may include an autonomous mode with a guidance program, a semi-autonomous mode and/or a manual mode with a remote console with user interface controls for directing the vehicle from a location remote Both scenarios can benefit from the present innovation. Humanoid robots can be located, identified, and communicated with as if a human operator. Human operators and humanoid robots may become someone interchangeable in the workplace, battlefield, or emergency scene. A simple, human interpretable communication of media can be made available which is tailored for the identified recipient, human or humanoid.

BEACONS. Beacons are taking the world by storm. They are low-powered radio transmitters that can send signals to smartphones that enter their immediate, vicinity, via Bluetooth Low Energy technology. In the months and years to come, we will see beaconing applied in all kinds of valuable ways. For marketers in particular, beacons are important because they allow more precise targeting of customers in a locale. A customer approaching a jewelry counter in a department store, for example, can receive a message from a battery-powered beacon installed there, offering information or a promotion that relates specifically to merchandise displayed there. In a different department of the same store, another beacon transmits a different message. Before beacons, marketers could use geofencing technology, so that a message, advertisement, or coupon could be sent to consumers when they were within a certain range of a geofenced area, such as within a one block radius of a store. However, that technology typically relies on GPS tracking, which only worsen outside the store. With beaconing, marketers can lead and direct customers to specific areas and products within a store or mall.

As a point of technical accuracy, the beacon itself does not necessarily contain messaging. Rather it sends a unique code that can be read only by certain mobile apps. Thus, the carrier of the smartphone has to have installed an, app. If not, no message will arrive. The choice to opt out exists at any time. But the key to beaconing's effectiveness is that the app does not actually have to be running to be awakened by the beacon signal. The present innovation contemplates that beaconing can enhance the entire mobile shopping puzzle. The technology is essentially invisible and can work without the mobile consumer having to do anything. Requiring the mobile consumer to take an action otherwise is a major hurdle for any mobile shopping technology. The shopper only has to agree in advance to receive such messages as they shop.

So imagine walking by or into a store and receiving a text message triggered by a beacon at the store entrance. It alerts you that mobile shoppers are eligible for certain deals, which you can receive if you want. Assuming you accept, you begin receiving highly relevant messaging in the form of well-crafted, full-screen images based on what department or aisle you are strolling through at the moment. Here is an example: implementing beaconing is less about installing the actual beacons and much more about rethinking the overall shopping experience they can help shape. The obvious application of beacon technology is to push content such as greetings, discounts and special offers, product information, branded content or other alerts.

Hospitals are increasingly relying on electronic tracking systems to keep tabs on equipment and lab specimens, and even to monitor the location of patients and staff. The use of the beacon system keeps patients and caregivers connected with wearable tracking devices using location-triggered messaging software. Patients simply wear a tracking device such as a wristband or badge that communicate anywhere there is a beacon. The system is able to track patients and view them on monitors, send alerts based on patient inactivity/activity levels, movement history and entry into restricted zones.

Mobile devices typically have a relatively minimal amount of display to aide mobility of the mobile device. Consequently, mobile devices may be dissatisfying to service provider representatives and consumers when used by the representatives to present data to consumers during in-person meetings. For instance, a doctor working on a wireless phone may find it frustrating when she sees charts, x-rays and other data regarding a patient's prognosis on her wireless phone, but cannot readily share the two-inch square display device of the phone with a patient. Likewise, a professor working on a tablet, such as an iPad® (iPad® is a registered trademark of Apple Inc.) may be frustrated when his slideshow is within seconds of reach on the iPad® for his own viewing, but he cannot readily display it to his classroom of students. Moreover, consumers often desire to modify the information presented to them or the service providers desire consumers to provide input on forms, presentations and other media.

Customers can act as beacons. Beacons can facilitate person-to-.person communication, which can be helpful for paging sales associates from within an app, rather than wandering around. Smart stores can dispatch sales associates to the right "department" based on their areas of expertise. Beacons can also support turn-by-turn directions to locate products. Combined with a voice or text search function, this can be very helpful for speedy grab-and-go shopping. In-store navigation can be useful if you have an app downloaded that syncs your Wish List or favorites, the ability to locate which ones actually exist in store, and to guide you to which products you'd like to view or purchase that day. There is also potential for "gamification", such as Easter egg hunts.

In store analytics based on beacons can provide more data on in-store behavior in order to optimize merchandising. The connection to mobile has potential for tying habits to customer segments, such as cross-channel buyers, frequent visitors, customers of a certain age or gender, or out-of-town visitors. A beacon can notify a retailer when an app-wielding customer enters the store. Beacons located near point-of-sale can interact with the customer's phone app to complete the transaction. The system can provide information regarding advantages of particular products that are tailored to background information associated with the customer.

Beacon technology is a step towards a closed-loop channel attribution where a marketer can measure the impact of mobile advertising exposure on in-store sales. For example, an e-commerce platform (through its mobile touchpoint) could pull location data based on a customer's proximity to a beacon, and match it to previous exposures of an ad. The overall system can address challenges to reliance on beacons, such as (1) attribution can be made across the segment of opted-in, tracked customers (incomplete data), and (2) beacons by themselves do not necessarily register human attention to a particular product. Proximity can be an indication of attention. Augmentation with eye tracking, for example, could bolster the information gained from proximity to a beacon.

Smartphone apps that leverage location data can improve the mobile experience; however, there are limits when the mobile device is indoors without access to a geospatial location system such as Global Positioning System (GPS). Beacons can provide a solution to this problem by using Bluetooth Low Energy (BLE) to allow sensors to detect, within inches, how close a smartphone is to the beacon. Beacons can be small enough to attach to a countertop or wall. Beacons can rely on battery-friendly, low-energy Bluetooth connections to transmit prompts or messages directly to a tablet or smartphone. This leaves them poised to transform how enterprises, transit systems, educational institutions, event organizers, and retailer communicate with people. It is a big step ahead that could open the door for groundbreaking services, which could enhance peoples' lives. Likewise, it may also create a new market for retailers who could use the technology to better target consumers.

One lingering question remains as to whether or not consumers will adapt to this new trend, as it teeters on the edge of "cool versus creepy". Beacon technology is still relatively new, leaving people to guess about its actual impact on both the marketing world and payments landscape. Many seem to think it could revolutionize consumerism. On the other hand, others predict big headaches along the way. But one thing is certain, mobile ads, or targeted offers and communications, are effective. Facebook just reported soaring revenue and profits resulting with 53% of $4^{th}$ quarter revenue associated with mobile advertisements. BLE seems like a natural extension in leveraging the mobile delivery channel with even more effective advertisements of any degree.

Using BLE-powered beacons, merchants could instantly become notified of your presence, pull up your profile, greet you by name and provide a personalized shopping experience. According to Bluetooth.com, by 2018, nine out of ten Bluetooth-enabled smartphones are expected to be Smart Ready devices. While consumer acceptance is still untested, a recent study commissioned by Swirl and ResearchNow found that 77 percent of consumers would be willing to share their smartphone location data, which is a prerequisite for beacon-triggered campaigns, as long as they receive enough value in return. That research also found that 65 percent of consumers are much more likely to entrust their location information to their favorite retailers than to shopping/deals apps, Google or Facebook.

That said, if BLE technology is the future of mobile payments and mobile marketing, merchants will need to be very cautious about their approach to avoid creeping out their consumers, as customers are already bombarded by irrelevant offers and a vast number of other communication types. The best way for merchants to accommodate this is by leveraging big data such as the retailer's CRM database and inventory management system, which will enable a merchant to analyze past spend patterns to make targeted offers based on product availability or inventory in a real-time manner. Although a more complex approach, that can be the best way to drive incremental sales.

For example, a very large national big box retailer presents or sends all consumers the same flyer with the same discount on a recurring basis. In one instance, the retailer does not require the consumer to bring in the coupon, as the cashier will just scan one already on-hand at the point-of-sale. If a retailer truly desires to drive incremental sales, the approach taken should be to provide product-specific discount at the individual level that are not advertised to the masses. If retailers do not take such a targeted approach, the retailer risks over-couponing for something that did not need to be discounted, which could actually cut into revenues and not increase them. Furthermore, consumers may quickly shy away from nationally. Based on an analysis by Hillshire's agency BPN, which is part of the IPG Mediabrands global network, there were 6000 in-store engagements in the first 48 hours of the two-month trial, and purchase intent increased 20 times. Shopper needed an app such as Epicurious, Zip List, Key Ring or Checkpoints. This beacon platform is run by InMarket. The present innovation can include use of GIMBAL Context Aware Platform, available from Qualcomm at http://www.gimbal.com.

A network architecture is described. In an implementation, a network architecture communicatively couples one or more mobile devices, each mobile device communicatively coupled to one or more presentation screens and one or more servers for improved visual communication during in-person meetings, teleconferences and virtual encounters. A presentation screen includes without limitation a television, a computer monitor, a high-definition television, an Internet television, and a projector and screen unit. In an implementation, the network architecture delivers location data regarding each of the mobile devices to the one or more servers. Various embodiments provide a network architecture configured to enable consumers, such as patients, to modify data presented on the presentation screens through a second mobile device.

Also provided are procedures for service providers to deliver presentations to consumers via a presentation screen that displays in substantially real-time certain data displayed on a service provider's mobile device. In an implementation, a presentation screen automatically reflects (or mirrors) certain displays on a service provider's mobile device when the mobile device is within a predetermined proximity of the presentation screen. In an implementation, a first mobile device is configured to project data displayed on the mobile device onto the presentation screen for a second device, such as a second mobile device or a server, configured to collect such data projected by the first mobile device. For example, a patient can fill out an electronic form with input data on the first mobile device (the patient's own mobile device or a mobile device provided to him) and have the data reflected on the presentation screen, which a second mobile device, such as that of a doctor or a nurse, or a hospital server can collect the input data.

To these and other ends, network architectures are described. In an implementation, a network architecture communicatively couples one or more mobile devices, each mobile device communicatively coupled to one or more presentation screens and one or more servers. A presentation screen includes without limitation a computer monitor, a high-definition television, Internet televisions (such as, ANDROID TV™ television (ANDROID™ is a trademark of Yen International, LLC) and APPLE TV® television (APPLE® is a registered trademark of Apple Inc.) for example), traditional televisions, and a projector and screen unit. In addition, presentation screens can themselves be mobile, and can employ solar technology or radio frequency harvesting to reduce energy costs. The use of a presentation screen employing solar technology, radio frequency harvesting and other alternate energy sources can enable presentations to occur in the absence of an electric outlet, or where available electric outlets are scarce.

Various embodiments include a network architecture configured to identify each of the devices, including presentation screens and mobile devices, communicatively coupled to the network, and to deliver location data regarding each of the mobile devices to the servers.

Also provided is a network architecture configured to enable service providers to deliver presentations to consumers via a presentation screen that mirrors certain displays on the mobile device in substantially real-time. Various embodiments provide a network architecture configured to enable consumers, such as patients, to modify data presented on the presentation screens through a second mobile device. In an implementation, a presentation screen automatically reflects certain displays on the mobile device when the mobile device is within a predetermined proximity of the presentation screen.

In addition, an integrated user interface on a mobile device is described. In an implementation, a mobile device includes a display device and one or more modules. The one or more modules are configured to display data represented in a user interface on the display device and on the presentation screen, automatically and without user interface. The data to be displayed on the presentation screen may be rendered by the mobile device or on one or more data sources communicatively coupled to the mobile device via a network. For example, the integrated user interface is configured to deliver slideshow presentations to consumers via a presentation screen, which mirrors in substantially real-time certain slideshow displays on the display device of the mobile device. In an implementation, an integrated user interface is configured to automatically reflect certain data displayed on a service provider's mobile device onto a presentation screen when the mobile device is communicatively coupled to the network and within a predetermined proximity of the presentation screen.

Various embodiments also include one or more fail-safe detection and prevention processes described herein to prevent sensitive data from reaching unintended recipients. A first fail-safe detection and prevention process of providing networked bracelets to users, such as patients, is provided to track the location of these users to detect their presence in relation to presentation screens before data is sent to the presentation screens. A second fail-safe detection and prevention process is effective to provide wire mesh or other radio frequency-canceling equipment to be installed to prevent the transfer of sensitive data from being distributed to unintended recipients. A third fail-safe detection and prevention process is effective to prevent the delivery of data to presentation screens upon the detection of two or more networked bracelets associated with the same secure wireless personal area network (WPAN) network. Further, certain modules, such as a send certain display module and a stop module, are provided to prevent certain data from being received by unintended recipients. The stop module may have various settings, such as stopping the sending of data to the presentation screen upon manual activation or automatically stopping the sending of data to the presentation screen after a selected period of time has expired.

Various embodiments include a network architecture including a master server configured to identify each of device, including presentation screens and mobile devices, communicatively coupled to the network, and to deliver location data regarding each of the mobile devices to the servers. Furthermore, the network architecture provides for the master server to be communicatively coupled to a subscriber database of recognized mobile devices. The master server organizes and operates the network, and recognizes devices by unique codes, such as an IP addresses, MAC addresses or other identifiers, stored in the subscriber database.

In the following discussion, a variety of example implementations of a mobile device (such as a mobile device having a touchscreen) are described. Additionally, a variety of different functionality that may be employed by the mobile device is described for each example, which may be implemented in that example as well as in other described examples.

FIG. 1 illustrates an example of an operating environment in which various principles described herein can be employed in accordance with one or more embodiments. A patient's private hospital room 100 is shown. On the wall is mounted a presentation screen 105, specifically a flat screen high-definition television, which a patient 110 watches while recovering from surgery. Other presentation screens can be used, and can be mobile or fixed within the hospital room. Furthermore, in some embodiments, presentation screens can employ solar technology to reduce energy costs. The use of a presentation screen employing solar technology or some other alternate energy source, such as radio frequency harvesting technology, can enable presentations to occur in the absence of an electric outlet, or where available electric outlets are scarce. In various embodiments, certain mobile devices utilize solar technology and/or radio-frequency harvesting technology to maximize battery life.

In the hospital room 100, a doctor 115 visits patient 110 to present post-operation instructions. The doctor creates a slideshow 125 of patient specific post-operation instructions on his mobile device 130 while in the hospital room. The display device of the mobile device 130 syncs with the presentation screen 105 to enable the doctor to present the instructions to the patient. In an example implementation, a portion of the display device of the mobile device 130 is displayed on the presentation screen 105, and in other implementations, the entirety of the display device is displayed on the presentation screen 105.

In an example implementation, the slideshow 125 resides on a database connected to the gateway server operating on a secure hospital network, such as an intranet. In this example, the doctor downloads the slideshow 125 from the database onto his mobile device 130 through the secure network, such as a password protected Wi-Fi® (Wi-Fi® is a registered trademark of the Wi-Fi Alliance) network. The mobile device 130 transmits the slideshow 125 to the presentation screen 105 through a short-range wireless network, such as a wireless personal area network (WPAN).

In an example implementation, the presentation screen 105 is a computing device equipped with modules and data of its own. In such implementations, the presentation screen 105 can come preprogrammed with certain standard forms and documents to be shared with individuals, such as patients.

Figure 2:
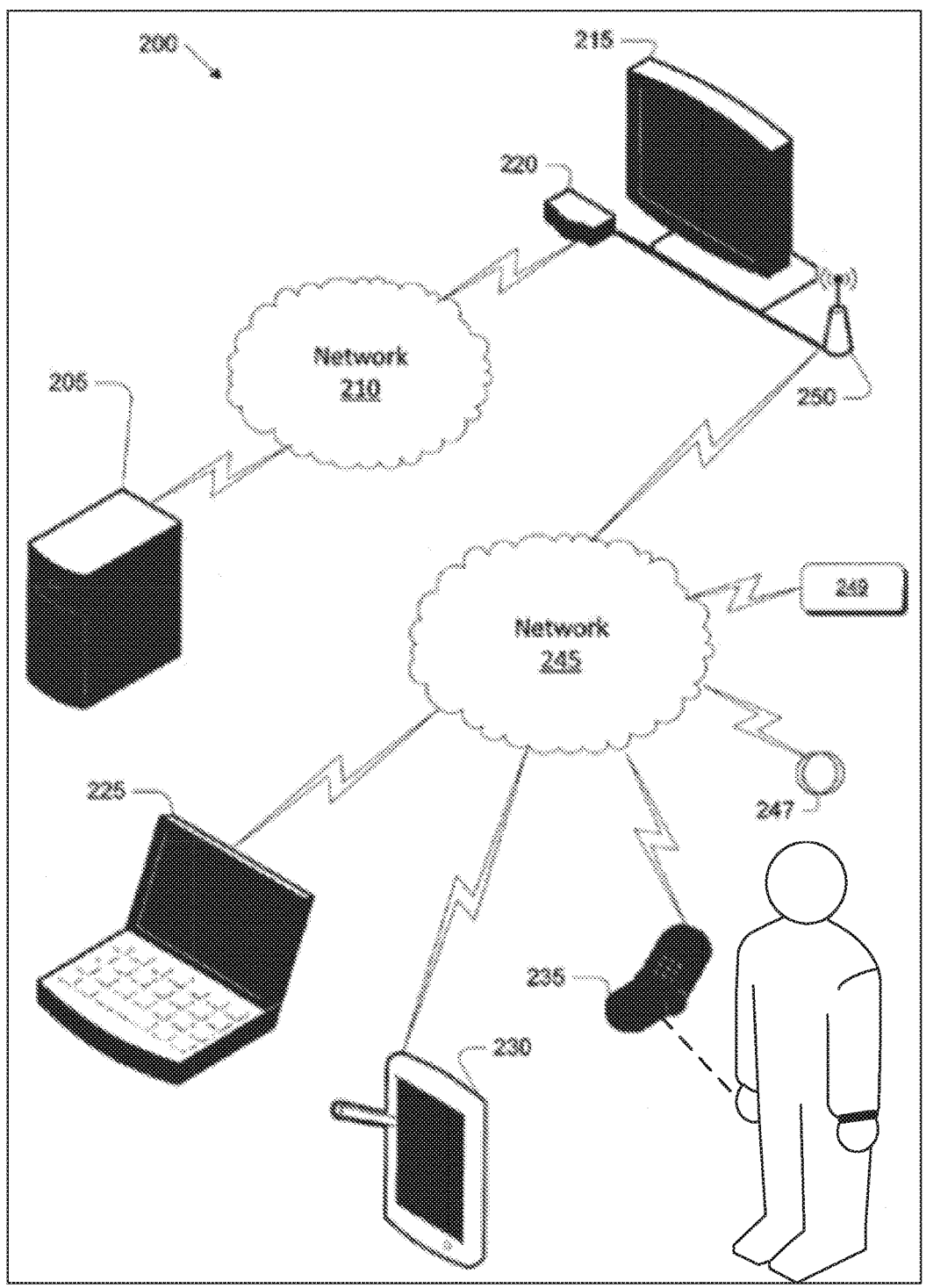
FIG. 2 illustrates an example network architecture in which various principles described herein can be employed in accordance with one or more embodiments.

FIG. 2 illustrates an example network architecture 200 in which various principles described herein can be employed in accordance with one or more embodiments.

In the example network architecture 200, server 205 is communicatively coupled through a secure local area network 210 to a presentation screen 215. Server 205 is a server-grade computing device, and can include several computing devices. The secure network 210 may be a local area network (LAN). The secure network may be wired (such as connected via Ethernet cables, for example) or may be a wireless network. In some implementations, a connective device 220 is used to connect the presentation screen 215 through secure network 210 to the server 205.

Mobile devices with display devices, such as a laptop 225, a tablet 230, and a mobile phone 235, communicate through a secure WPAN network 245 with the presentation screen 215. In addition to mobile devices with display devices are tracking devices, such as bracelet 247 and smartcard 249, such as an RFID enabled shopper loyalty card or a RFID enabled credit and/or debit card. Tracking devices do not have display devices. For clarity, mobile devices with display devices can generate location data that can be tracked by server 205. In an example implementation, the network architecture enables the mobile devices to project one or more images on its display device onto the presentation screen 215 through the secure WPAN network 245. In an example implementation in a retail environment, the network architecture enables a server to track the location of a shopper as she enters a display area in a store with a smartcard 249 and enables the server to project marketing content specifically tailored to the shopper onto a presentation screen at a point-of-purchase display in the store.

An example implementation of secure WPAN network 245 is a password protected Wi-Fi® network. An example implementation of WPAN network 245 includes a ZIGBEE® communication network which operates within the Institute of Electrical and Electronics Engineers (IEEE) 802.15.4 communication protocol (ZIGBEE® is a registered trademark of the Zigbee Alliance Corporation). The ZIGBEE® protocol operates in the industrial, scientific and medical (ISM) radio bands; i.e., 868 MHz in Europe, 915 MHz in the USA and 2.4 GHz in most other jurisdictions worldwide. ZIGBEE® technology is intended to be simple, inexpensive and readily maintainable. Likewise, the wireless network connecting the tablet to the television can also be a typical BLUETOOTH® communication network, which was used as the basis for the IEEE 802.11 communication protocol (BLUETOOTH® is a registered trademark of Bluetooth Sig, Inc.). Other wireless networks are also contemplated.

WPAN networks enable WPAN-equipped devices to communicatively couple to each other when they are in close proximity to one another. For example, when the mobile device comes into close proximity (such as within several meters, for example) of the presentation screen 215, the mobile device can communicate with the presentation screen 215 through the WPAN network 245 as if connected by a cable. In an implementation, when the mobile device couples to the WPAN network 245 it locks out other devices selectively, preventing needless interference and unauthorized access to information.

In an implementation, a first mobile device, such as laptop 225, is configured to project data displayed on the first mobile device onto the presentation screen 215 for a second device, such as tablet 230, configured to collect such data projected by the first mobile device. For example, a patient can fill out an electronic form with input data on the first mobile device (the patient's own mobile device or a mobile device provided to him) and have the data reflected on the presentation screen 215, which a second mobile device, such as that of a doctor or a nurse, or a hospital server, such as server 205, can collect the input data from the patient.

In implementations employing presentation screens 215 that are not WPAN-enabled off-the-shelf, the presentation screen 215 is physically coupled to a digital media receiver 250 or similar receiver to enable presentation screen communication over secure network 245. The digital media receiver 250 is equipped with one or more radio receivers and one or more transmitters to communicate with other devices, such as the mobile devices, on the WPAN network 245. In selected embodiments, the digital media receiver 250 is housed within the connective device 220. Having described an example network architecture 200, consider now a discussion of another example network architecture.

In an example implementation, server 205 tracks the location of bracelet 247 and smartcard 249 within the operating environment as these tracking devices connect to various WPAN networks, including WPAN network 245. The server can be associated with a subscriber database that provides unique device numbers with the devices' associated users. For example, an account owner named Jane Doe enters a financial institution with a smartcard 249, which in this example is a debit card enabled with an RFID chip. Through the network association of smartcard 249 with WPAN network 245 in the financial institution, the server 205 recognizes that Jane Doe has entered the financial institution, recognizes her location, and delivers certain data, such as marketing materials customized to Jane Doe, to a presentation screen 215, which is in close proximity to Jane Doe.

In another example implementation, the bracelet 247 is provided to a patient in a hospital. The presumed location of the bracelet 247 is tracked by server 205 through network 245 and network 210.

Figure 3:
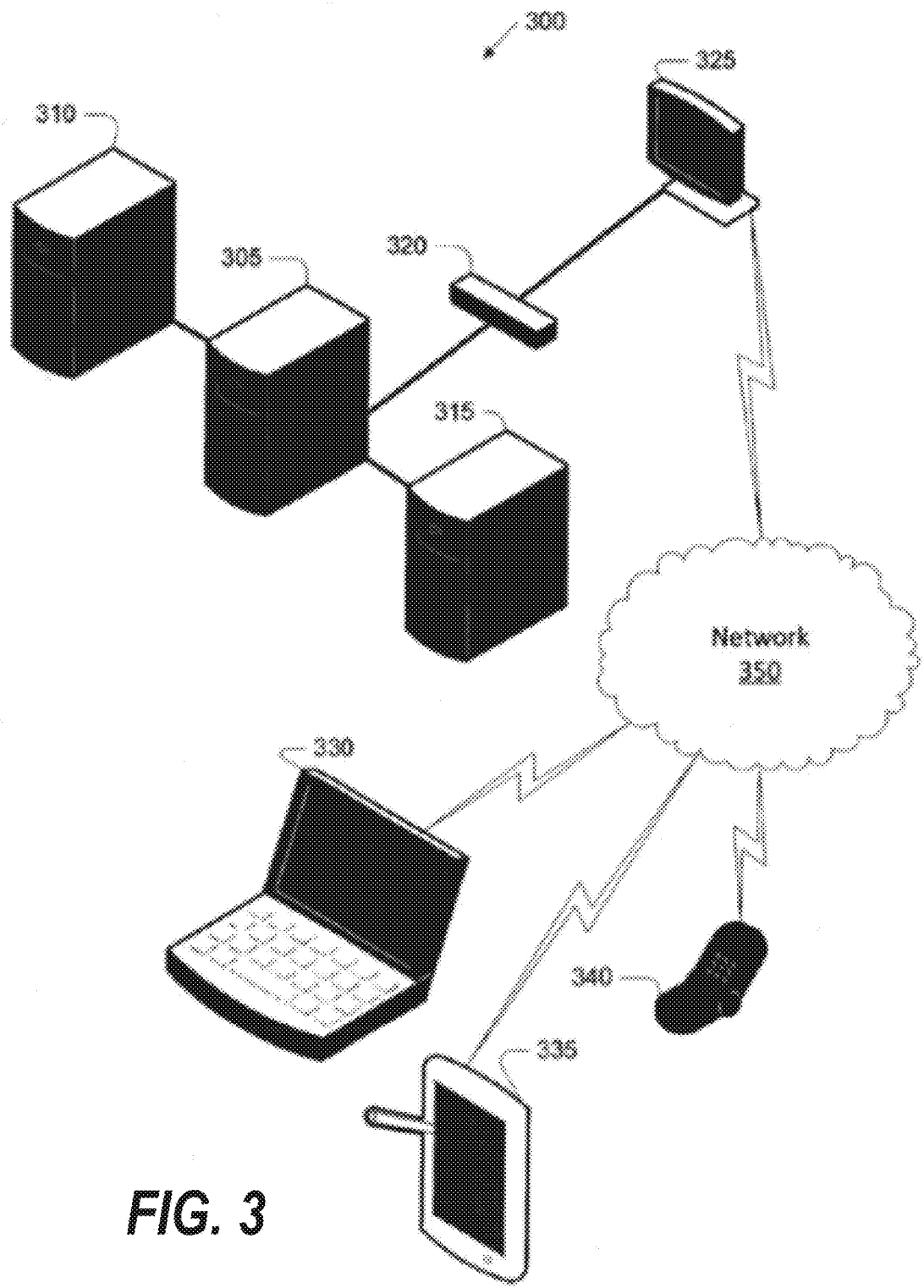
FIG. 3 illustrates an example network architecture in which various principles described herein can be employed in accordance with one or more embodiments.

FIG. 3 illustrates an example network architecture 300 in which various principles described herein can be employed in accordance with one or more embodiments. In the example network architecture 300, a gateway server 305 is coupled to second server 310 and a third server 315. The gateway server is connected to a switch 320 and through cables, such as Ethernet cables, to one or more presentation screens 325.

Mobile devices, such as a laptop 330, a tablet 335, and a mobile phone 340, communicate through a secure WPAN network 350 with the presentation screen 325. In an example implementation, the network architecture is configured to enable a mobile device to display one or more images from its display device onto the presentation screen through the secure WPAN network 350 in substantially real-time.

Figure 4:
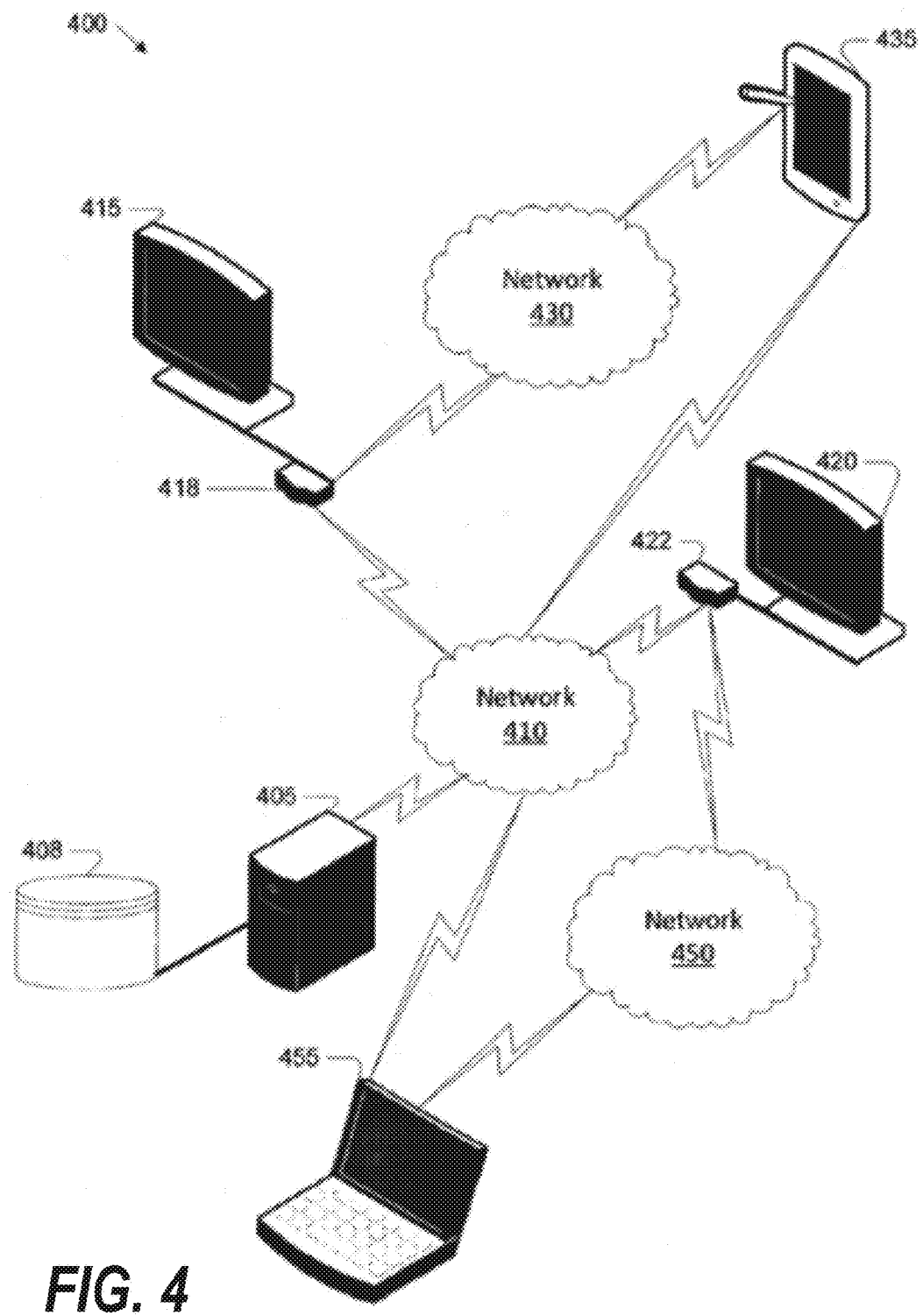
FIG. 4 illustrates an example network architecture illustrating multiple presentation screens, each with its own wireless personal area network (WPAN), in which various principles described herein can be employed in accordance with one or more embodiments.

Having described an example network architecture 300, consider now a discussion of another example network architecture. FIG. 4 illustrates an example network architecture 400. In the example network architecture 400, a server 405 is coupled to a wireless network 410. Server 405 is a master server, which organizes and operates wireless network 410, and recognizes networked devices, including mobile devices and presentation screens, by their unique identification codes, such as IP addresses, stored in a subscriber database 408 associated with the server 405. The subscriber database 408 associates the unique identification codes of each networked devices with users. For example, a presentation screen in a certain hospital room is associated with the patient assigned to that room. The subscriber database 408 can be housed within server 405 or communicatively coupled to server 405 through an Ethernet cord, or through an external network, such as the Internet, on the occasions that the subscriber database 408 is stored with an enterprise server at a remote location, such as an enterprise headquarters. Examples of the subscriber database 408 include without limitation a database of healthcare professionals, a loyalty reward program database, a social network database, and so on. Wireless network 410 may be of any suitable type for data transfer, such as Wi-Fi®.

The server 405 communicates over wireless network 410 with a first presentation screen 415 through a first connective device 418 and a second presentation screen 420 through a second connective device 422. The connective devices 418, 422 can be integrated into the internal hardware of the presentation screen 415, 420, rendering the presentation screens networked devices, or each of the connective devices 418, 422 can be an external hardware component that is physically connected to the presentation screen.

In this example network architecture 400, each presentation screen has its own secure wireless network on its own identifiable radio frequency. Independent secure wireless networks for each presentation screen enables mobile devices to securely push data from the mobile devices or request data from server 405 to be projected onto particular presentation screens while other presentations screens remain available for presentations delivered by other mobile devices on separate secure wireless networks. Connective devices 418, 422 are equipped to communicate via a second secure wireless network, such as Bluetooth, for proximity based communication and location detection of the mobile devices. As discussed above, connective devices 418, 422 are housed within the presentation screens 415, 420, for example, when the presentation screens 415, 420 are networked televisions. Thus, a first mobile device 435 communicates through the first connective device 418 and through a first secure WPAN network 430 with first presentation screen 415.

In an example implementation of the example network architecture 400, the first mobile device 435 is configured to activate a display of data stored in connection with the server 405 on the first presentation screen 415 through wireless network 410. In an example implementation of the example network architecture 400, the first mobile device 435 is configured to deliver in substantially real-time data generated on the first mobile device 435 through wireless network 410 to the first presentation screen 415. In an example implementation of the example network architecture 400, the first mobile device 435 is configured to deliver in substantially real-time data generated on the first mobile device 435 through the first secure WPAN network 430 to the first presentation screen 415.

Because the server 405 recognizes the IP address of the first mobile device 435 and recognizes that it is communicatively coupled to a first presentation screen 415 through secure WPAN network 430, responsive to a data request of the first mobile device 435, the server 405 delivers data to the first presentation screen 415 securely over wireless network 410 to the first presentation screen 415 and not to other presentation screens connected to the wireless network 410.

In an example implementation, the data presented on the first presentation screen 415 is associated with a user identified as assigned to the room in which the first presentation screen 415 is located. The server 405 identifies users associated with each device through the subscriber database 408. For example, as a doctor with the first mobile device 435, which previously associated with wireless network 410 upon the doctor's arrival to a hospital with the first mobile device 435 in operation mode, enters a first patient's room in which the first presentation screen 415 is located, the first mobile device 435 associates with the first secure WPAN network 430, and data associated with first patient is displayed upon the first presentation screen 415. Such data can be stored on a database associated with server 405 and is triggered to be sent to the first presentation screen 415 by a request sent to the server 405 from the first mobile device 435. According to settings on the first mobile device 435, the data request can be automatically sent as the first mobile device associates with the secure WPAN networks 430, 450.

In an example implementation, as a data request is received by server 405, a response is prepared and delivered to the requested destination in substantially real-time. Hence, as the first mobile device 435 is in close proximity to the first secure WPAN network 430 in the first hospital room with the first presentation screen 415 and a first patient is assigned to the first hospital room equipped, the server 405 delivers certain electronic medical records associated with the first patient automatically to the presentation screen according to a module on the first mobile device. According to settings on the first mobile device 435, data requests to be presented on the presentation screen can be sent manually, and a subset of user data can be delivered automatically or manually. Various fail-safe detection and prevention processes are described herein and will be described in turn.

Continuing with the example implementation described above in connection with FIG. 4, according to a first fail-safe detection and prevention process, the data associated with the first patient is sent to the first presentation screen 415 upon the server 405 discovering that a networked bracelet (such as bracelet 247 in FIG. 2) assigned to the first patient is associated with the first secure WPAN network 430. In this example implementation, if the first patient is associated with the first secure WPAN network 430, then the first patient is in the first hospital room, since the first secure WPAN network 430 has a small range.

In selected embodiments, according to a second fail-safe detection and prevention process, wire mesh or other radio frequency-cancelling equipment can be installed to prevent sensitive data from being distributed to unintended recipients. In selected embodiments, a third fail-safe detection and prevention process can be implemented.

The third fail-safe detection and prevention process includes sending a delivery failure message to the first mobile device 435 upon receiving a data request at the server 405 on the event that the server 405 detects two or more networked bracelets associated with the first secure WPAN network 430. This third fail-safe detection process is useful when two or more patients are placed in a single hospital room with a single presentation screen that is viewable by all patients in the hospital room.

Various embodiments provide for any combination of the above-described fail-safe detection and prevention processes to be employed in a network architecture. Further still, no fail-safe detection and prevention process may be employed in a network architecture.

In addition, a second connective device 422 communicatively couples the presentation screen 420 with a second secure WPAN network 450. A second mobile device 455 is connected to second secure WPAN network 450. In an example implementation, as the second mobile device 455 is placed within range of the second secure WPAN network 450, certain data displayed on the second mobile device 455 is automatically forwarded through wireless network 410 to the second presentation screen 420. In an example implementation, according to settings on the second mobile device 455, as the second mobile device 455 is placed within range of the second secure WPAN network 450, certain data displayed on the second mobile device 455 is automatically forwarded through the second WPAN network 450 to the second presentation screen 420.

The second mobile device 435 will not present materials onto the second presentation screen 420 without activation of certain modules and settings on the second mobile device 435 to recognize the second secure WPAN network 450. Thus, each mobile device in the example network architecture 400 securely sends data to its respective presentation screen. Such an implementation is useful where privacy is of concern, such as in the sharing of (1) medical records to patients in hospital rooms, (2) financial records in conference rooms in financial institutions, and (3) medical and educational records by counselors and advisors in educational institutions.

Figure 5:
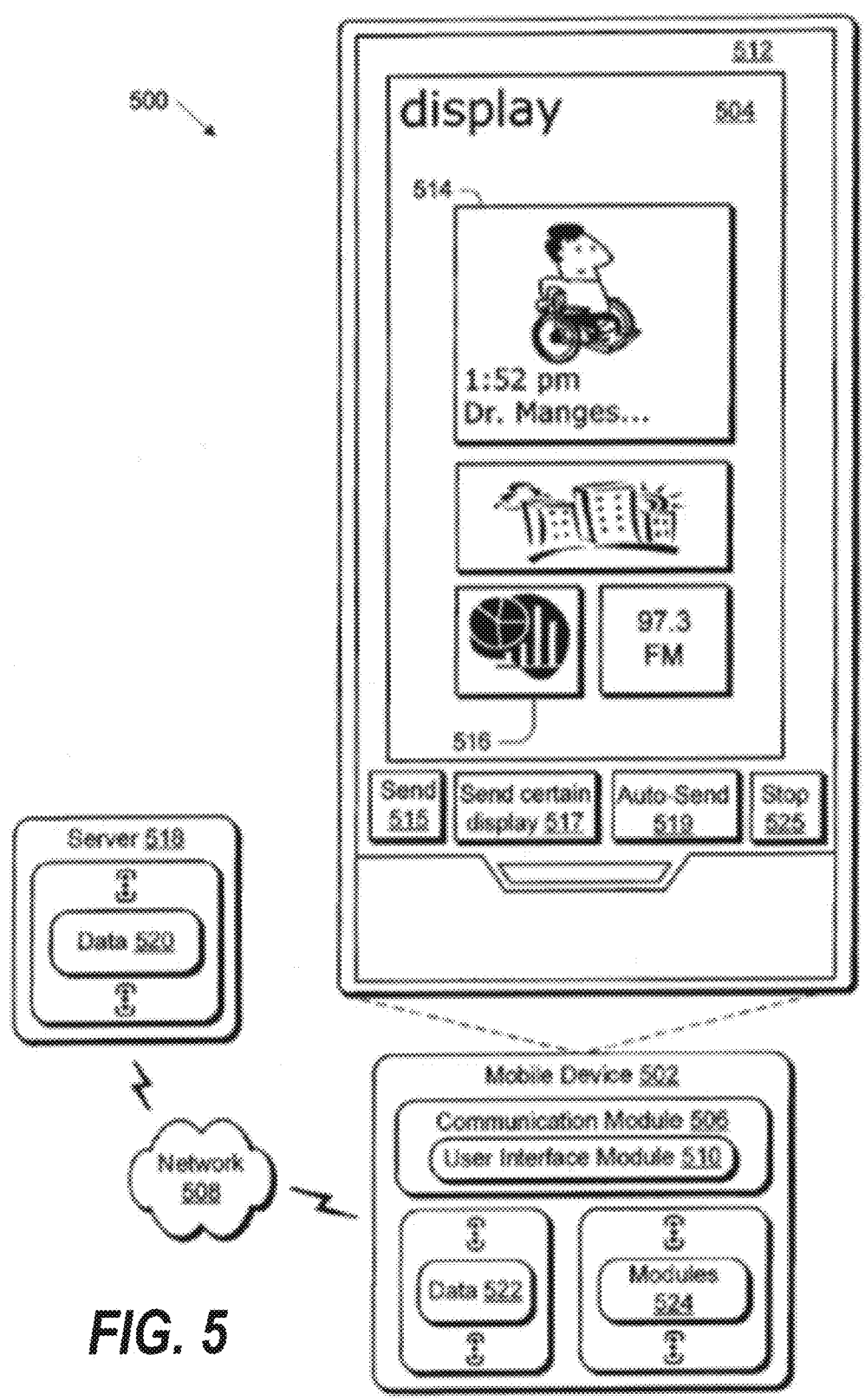
FIG. 5 is an illustration of an example implementation of a mobile device in accordance with one or more embodiments of devices, features, and systems for rendering media, according to one or more embodiments.

FIG. 5 is an illustration of an example implementation 500 of a mobile device 502 in accordance with one or more embodiments of devices, features, and systems for selecting data. The mobile device 502 includes a display device 504 that may be used to output a variety of content, such as a caller identification (ID), electronic medical records, contacts, images (such as photos, x-rays, graphs, charts, slideshows, for example) as illustrated, email, multimedia messages, Internet browsing, game play, music, video and so on. In an implementation, the display device 504 is configured to function as an input device by incorporating touchscreen functionality, e.g., through capacitive, surface acoustic wave, resistive, optical, strain gauge, dispersive signals, acoustic pulse, and other touchscreen functionality. For example, mobile device 502 includes laptops, mobile phones, tablets and personal digital assistants.

The mobile device 502 is also illustrated as including a communication module 506. The communication module 506 is representative of functionality of the mobile device 502 to communicate via a network 508, e.g., via browser functionality. In another example, the communication module 506 may include telephone functionality to make and receive telephone calls. The communication module 506 may also include a variety of other functionality, such as to capture content, form short message service (SMS) text messages, multimedia messaging service (MMS) messages, emails, status updates to be communicated to a social network service, conduct telephone calls, and so on. A variety of other examples are also contemplated, such as producing financial records, financial plans, educational records, educational presentations, demonstratives, and medical records.

The mobile device 502 is also illustrated as including a user interface module 510. The user interface module 510 is representative of functionality of the mobile device 502 to generate, manage, and/or output a user interface 512 for display on the display device 504. A variety of different techniques may be employed to generate the user interface 512 such that the user interface 512 may provide a variety of functionality.

For example, the user interface module 510 may configure the user interface 512 to act as an integrated data hub for the display device 504 and a presentation screen (such as presentation screen 215 of FIG. 2). For instance, the user interface 512 includes a first window 514 that includes representations of data, in this event an image of a man in a wheelchair, produced by the mobile device 502.

As an integrated data hub, the user interface 512 may represent data from a variety of different sources. For example, a second window 516 in the user interface may represent data that is accessible by the mobile device 504 via the network 508, such as from a server 518 having one or more items of data 520. The data 520 may take a variety of forms, such as electronic medical records, which include photographs of x-rays, charts, graphs, forms and documents. For example, the data 520 from the server 518 reflected in a second window 516 includes charts and graphs. The data 520 may also be representative of data that is available for download over the network 508 for local storage on the mobile device 502, which may be represented as data 522. In another example, other portions may be provided such as financial records, educational slideshows, articles, and so on that are not specific to the mobile device 502 but instead are provided by a service provider, e.g., the server 518. Thus, a wide variety of different data may be represented in the user interface 512 by the user interface module 510.

The mobile device 504 is configured to display its data on a presentation screen (see FIGS. 1-4). The mobile device 504 is configured to display the data of the entire display device 504 to the presentation screen when the "send" module 515 is selected. The mobile device 504 is also configured to send a smaller portion of the display device 504, such as just the data displayed in window 514 or the data shown in window 516 to the presentation screen. The "send certain display" module 517 is configured to send less than the entire display device 504 to the presentation screen upon activation. In addition, all or a portion of the display device 504 may be presented on the presentation screen upon activation of the "auto-send" module 519. Also, a "stop" module 525 is provided which is configured to stop the sending of data to the presentation screen for display thereon upon activation of the stop module 525.

Further in the description of FIG. 5, to provide a wide variety of different data in a variety of media ultimately to the presentation screen, the user interface module 510 may leverage one or more modules 524, which may be configured to render particular types of data. For example, one of the modules 524 may be configured to render charts and graphs, another one of the modules 524 may be configured to fetch and render streaming data 520 over the network 508, and so on. Thus, the user interface module 510 may configure the user interface to include representations of data from a variety of different sources and provide access to the data through a variety of different modules 524. Further, through the send module 515, send certain display 517 and auto-send module 519, the user has options for delivering data to the presentation screen. In this way, the user interface 512 integrates this data to be selectable for rendering in a single view on the presentation screen.

Figure 6A:
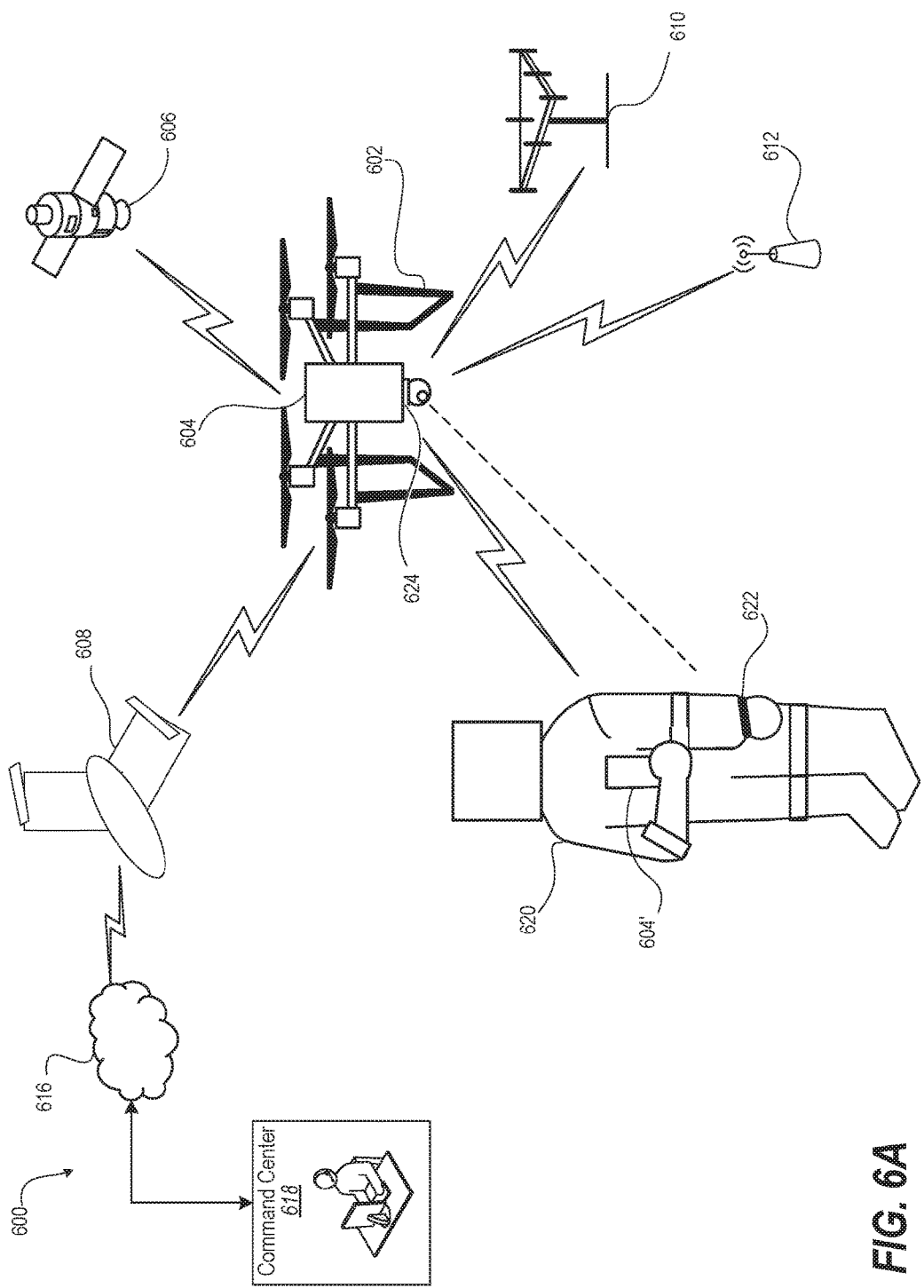
FIG. 6A and FIG. 6B illustrate a communication system in which further mobility and flexibility is introduced by remotely controlled, semi-autonomous or autonomous vehicles, either ground, air or water-based, according to one or more embodiments.
Figure 6B:
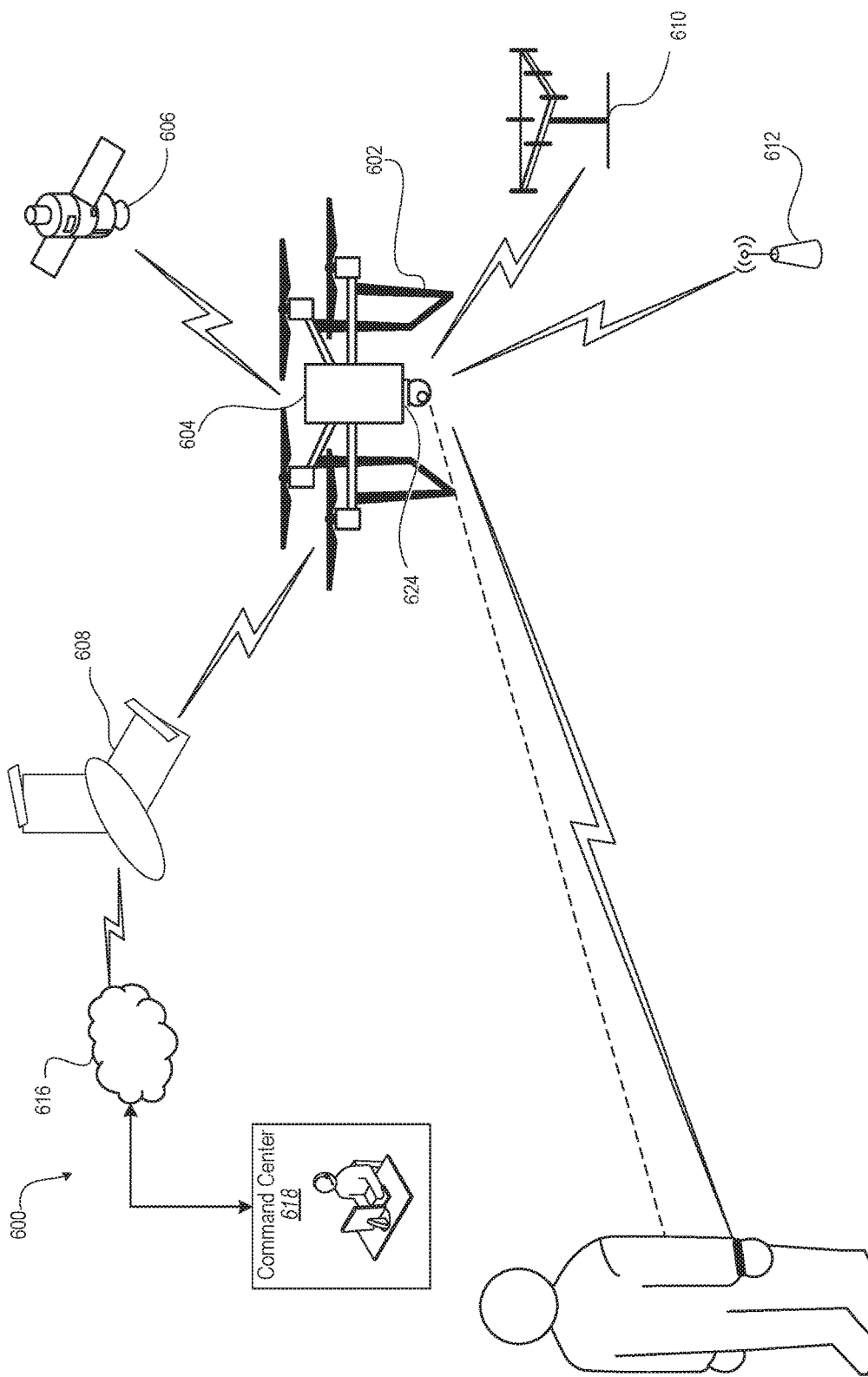

FIG. 6A and FIG. 6B illustrate a communication system 600 in which further mobility and flexibility is introduced by remotely controlled or autonomous vehicles, either ground, air or water-based, including an unmanned vehicle (UV) 602 and a computing device 604. An unmanned vehicle (UV)

602 may include any known UV, such as an unmanned aerial vehicle (UAV) (e.g., a drone), an unmanned aerial system (UAS), an unmanned surface vehicle (USV), an unmanned ground vehicle (UGV), unmanned underwater vehicle (UUV), and the like. As will be appreciated, UV 602 may be configured to travel via land, sea, sub-sea, air, or any combination thereof. As will be appreciated, UV 602 may be used for performing a wide range of tasks.

In one example, one or more UVs may connect to an application program, such as Petrel®, using a framework, such as Ocean® framework directly. In another example, the one or more UVs may connect to an application program using a web service, such as Ocean® Web service (also owned by Schlumberger). The UVs may then link into the framework. Plug-ins, which may be custom built, may be configured to analyze and process the data captured by the UVs. The data, which may comprise, as non-limiting example, images, a video stream, GPS locations, and air quality data, may be shared with other environments, such as Studio®, on other platforms, such as AVOCET® or TECHLOG®, based on their respective domains.

UV 602 may include one or more imaging or sensing devices for capturing data. Sensing devices may be coupled to UV 602 or may be internal to UV 602. As non-limiting examples, sensing devices may include cameras, location sensors (e.g., GPS sensors), electromagnetic spectrum sensors, gamma ray sensors, biological sensors, chemical sensors, thermal sensors, geophones, etc. UV 602, and more specifically, sensing devices, may be configured to capture, for example, time-dependent (e.g., variant) data, environmental data, or both. Time-dependent data may be associated with one or more geographical locations, which may include one or more areas of interest. The time-dependent data may also be associated with, for example, a production operation, a pipeline, flaring, and the like. Environmental data may include, for example only, seismic data, drilling data, surface images, or other types of data where the location varies but time may remain generally constant.

The imaging system of the present invention in particular embodiments may be configured to provide still images and/or video, mono or stereo, transmitted in real-time and/or recorded on accessible media for later retrieval and analysis.

The network may include the Internet or any other network capable of communicating data between devices. Suitable networks may include or interface with any one or more of, for instance, a local intranet, a PAN (Personal Area Network), a LAN (Local Area Network), a WAN (Wide Area Network), a MAN (Metropolitan Area Network), a virtual private network (VPN), a storage area network (SAN), a frame relay connection, an Advanced Intelligent Network (AIN) connection, a synchronous optical network (SONET) connection, a digital T1, T3, E1 or E3 line, Digital Data Service (DDS) connection, DSL (Digital Subscriber Line) connection, an Ethernet connection, an ISDN (Integrated Services Digital Network) line, a dial-up port such as a V.90, V.34 or V.34bis analog modem connection, a cable modem, an ATM (Asynchronous Transfer Mode) connection, or an FDDI (Fiber Distributed Data Interface) or CDDI (Copper Distributed Data Interface) connection. Furthermore, communications may also include links to any of a variety of wireless networks, including WAP (Wireless Application Protocol), GPRS (General Packet Radio Service), GSM (Global System for Mobile Communication), CDMA (Code Division Multiple Access) or TDMA (Time Division Multiple Access), cellular phone networks, GPS (Global Positioning System), CDPD (cellular digital packet data), RIM (Research in Motion, Limited) duplex paging network, Bluetooth radio, or an IEEE 802.11-based radio frequency network. The network 110 can further include or interface with any one or more of an RS-232 serial connection, an IEEE-1394 (Firewire) connection, a Fiber Channel connection, an IrDA (infrared) port, a SCSI (Small Computer Systems Interface) connection, a USB (Universal Serial Bus) connection or other wired or wireless, digital or analog interface or connection, mesh or Digi networking. The network may be a network of data processing nodes that are interconnected for the purpose of data communication. The UV system may communicate with the GPS satellite via the network to exchange data on a geographical location of the UV system.

For the purposes of communication, the UV may be compatible with one or more of the following network standards: GSM, CDMA, LTE, IMS, Universal Mobile Telecommunication System (UMTS), 4G, 5G, 6G and upper, RFID, and so forth. In some embodiments, the UV may have an operating system executing on the processor. The operating system may include Android, iOS, Firefox OS, and other operating systems.

In one embodiment, an unmanned vehicle such as an unmanned aerial vehicle (UAV) 602 by carrying a mobile device 604 that communicates within the communication system 600 using one or more modalities. For example, the mobile device 604 can communicate with a communication satellite 606, or an atmospheric satellite UAV such as Titan/Google Solara 50 or other airborne networks or swarming aerial vehicle network 608, a cellular LTE access network 610, wireless access points/radios 612 or to another mobile device 604', such as smartphone carried by a robotic agent 620 that is capable of understanding and complying with human interpretable commands. One or more of these communication connections can further communicate to a network 616, such as the Internet, cellular network or other communication network including ad hoc mesh networks, which in turn communicates with other users, depicted as a command center 618. The mobile device 604 of the UAV 602 can authenticate through the network 616.

In one or more embodiments, the UAV 602 can operate using control instructions derived from the Open Source Dronecode Project 24 that was launched by Linux Foundation or other open source system code. The Project brings together existing open source drone projects and assets under a nonprofit structure governed by The Linux Foundation. The result is a common, shared open source platform for unmanned systems. Dronecode includes the APM software platform and associated code, which until now has been hosted by 3D Robotics.

In one or more embodiments, the UAV 604 tracks and follows the robotic agent 620 by tracking a beacon or radio frequency identification (RFID) device, depicted as a bracelet 622. Alternatively or in addition, the unmanned system can acquire and track the robotic agent 620 using sensors such as infrared sensors (IR), electro-optical (EO) sensors and radar as well as other video sources 624. The UAV 602 can be deployed to perform tasks such as physical security, crowd control and public safety, intelligence, surveillance, reconnaissance and other law enforcement tasks etc., under the direction of the command center 618. Operations of such a communication system 600 can be extended unmeasurable distance by building different types of networks to include mobile ad-hoc networks, or all systems communicating back to the control center 618 at any given time. The communication system 600 can be dynamically configured for areas not served by traditional network internet access or highspeed data links such as in remote areas during an emergency situation following a natural or manmade disaster or by the lack of infrastructure.

The authentication abilities of the UAV 604 can provide for singling out individuals or mobile vehicles that are visually or otherwise detected for but which an authenticating mobile device is not present. For example, the communication system 600 can focus security efforts on those entities that are unknown to the communication system 600 and could pose a threat.

According to yet one implementation, the apparatus further includes a swarm control module configured to compute one or more control commands for the local vehicle to cooperate as a swarm with the plurality of vehicles.

The swarm control module, in one embodiment, is configured to generate control commands (e.g., velocity and positional commands) and/or waypoints for the local vehicle to cooperate as a swarm with the plurality of vehicles. The plurality of unmanned vehicles, in some embodiments, are configured to operate as a swarm to coordinate performance of tasks or mission elements. In some embodiments, the swarm control module selects a formation for the plurality of vehicles and computes guidance commands configured to cause the local vehicle to travel in the selected formation. In some embodiments, the swarm of vehicles is assigned a group task, the guidance commands selected to accomplish the group task. The swarm control module may coordinate activities, including positions and velocities, among the swarm while accomplishing the group task. In certain embodiments, the swarm control module receives a group waypoint, wherein the guidance commands are selected to bring the swarm (including the local vehicle) to the group waypoint.

In some embodiments, the swarm control module gathers data regarding the local vehicle, for example via the position sensor and/or the health sensor. For example, the swarm control module may monitor data regarding the local vehicle's position, heading, velocity, and acceleration. The swarm control module may further obtain data relating to relative distances between the local vehicle and others of the plurality of unmanned vehicles. The swarm control module then computes in real-time guidance commands, for example using flight control algorithms stored in the memory. In certain embodiments, the guidance commands are then sent to the autopilot. In certain embodiments, the swarm control module sends the waypoints to the guidance module for planning a path based on the generated waypoints.

An embodiment of the invention comprises a gateway modular device and data management system that encompasses such capability as, for example, duplex-directional multimedia networking, power optimization, dynamic configuration, communications, and data management, while operating within a variety of devices and network topologies. The gateway serves as a functional model for device automation, modular system and data management, data channeling, paired, grouped and/or networked device optimization, and hands-free and remote systems control, Although technically an operating system, the gateway may be more accurately defined as a device, data and network optimization and control system, one or more embodiments of the invention of the Gateway Control System (GCS) comprises a virtual machine monitor that is configured to run in an embedded system as a downloadable program or as a networked application. One or more embodiments of the invention comprises a multitasking control system that is capable of functional expandability, portability to various operating environments, and interoperability with existing operating systems.

Gateway Control System

Functional capabilities within the herein disclosed gateway are performed in both a local and a networked topology using local and remote hardware and software. Software within an embodiment of the gateway is partitioned into sequentially, autonomous code, referred to herein as "modules," each module being configured to communicate with hardware and other gateway modules. Collectively, all gateway modules are referred to herein as the gateway stack (GS). Each member of the GS can be turned on or off, downloaded from a remote site, and dynamically configured.

In the Gateway control system, device optimization is managed in an intelligent semi-autonomous modular architecture with each module selecting the most effective method for accomplishing each task based on user configurations for power, data, device, network, security, and communications. Different sets of systems and tasks, such as power management, data management, voice command and communications, Audio-Video Systems, and Geographic and Contextual Systems, and all related hardware, programs and components are organized into standard, virtual modular management systems.

Figure 7:
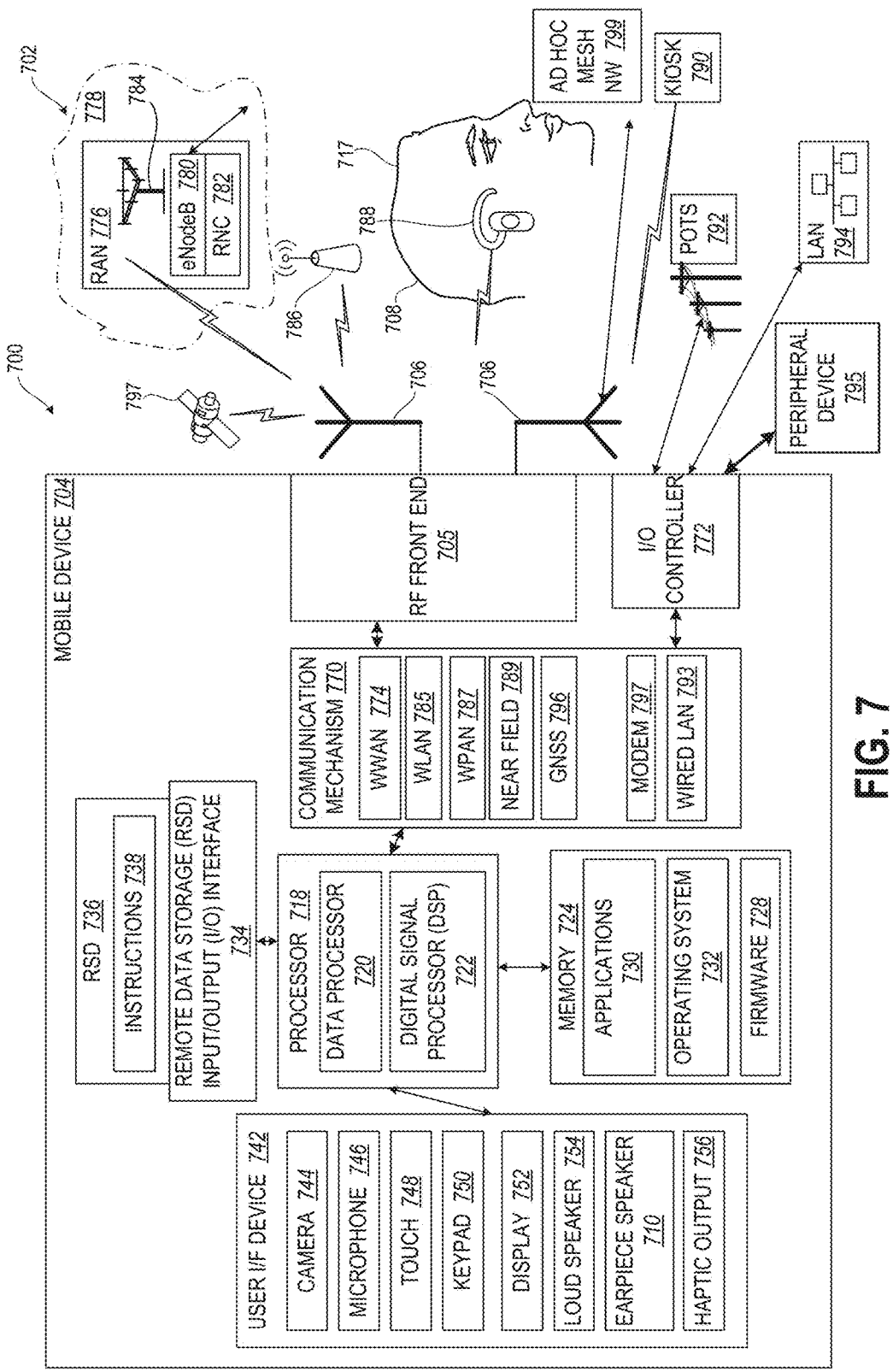
FIG. 7 illustrates an example communication system that includes a mobile device, according to one or more embodiments.

Turning now to FIG. 7, there is depicted a block diagram representation of an example communication system 700 that includes a mobile device 704 within which several of the features of the disclosure can be implemented. In an exemplary aspect, the mobile device 704 includes the hardware and software to support the various wireless or wired communication functions as part of a communication system 702. According to the general illustration, the mobile device 704 includes a radio frequency (RF) front end 705 that transmits via one or more antennas 706. The example mobile device 704 can output audio to a user 708 via earpiece speaker 710 during a two-way communication session. The earpiece speaker 710 is oriented to be placed to the user's 708 ear and outputs audio at a volume appropriate for this proximity.

Referring now to the specific component makeup and the associated functionality of the presented components, the mobile device 704 can include an integrated circuit (IC) processor 718. The processor 718 can include one or more programmable microprocessors, such as a data processor 720 and a digital signal processor (DSP) 722, which may both be integrated into a single processing device, in some embodiments. The processor 718 controls the communication, user interface, and other functions and/or operations of the mobile device 704. These functions and/or operations thus include, but are not limited to, application data processing and signal processing. The present innovation can be implemented using hardware component equivalents such as special purpose hardware, dedicated processors, general purpose computers, microprocessor-based computers, micro-controllers, optical computers, analog computers, dedicated processors and/or dedicated hard wired logic. The mobile device 704 can be one of a host of different types of devices, including but not limited to, a mobile cellular phone or smart-phone, a cordless phone, a desktop computer, a laptop, a net-book, an ultra-book, and/or a tablet computing device.

Memory 724 is connected to processor 718 and may include volatile memory and/or non-volatile memory that store software code such as software 726 and/or firmware 728. One or more executable applications 730 can be stored within memory 724 for execution by the processor 718. The memory 724 may be augmented by data storage, illustrated as a removable storage device (RSD) input/output (I/O) interface 734 that receives a RSD 736 containing data or executable instructions 738. The associated functionality and/or usage of each of the software modules will be described in greater detail within the descriptions, which follow.

Mobile device 704 includes input/output (I/O) devices 742 for interacting with the user 708. The I/O devices 742 can include one or more input devices, such as camera 744, microphone 746, touch screen and/or touch pad 748, and keypad 750. The I/O devices 742 can also have one or more output devices, such as display 752, loudspeaker 754, the earpiece speaker 710, and haptic output device 756.

A communication mechanism 770 can convert information from the processor 718 or an appropriate communication protocol for wireless transmission by the RF front end 705 or wired transmission by an I/O controller 772. The communication mechanism can convert a received communication signals encoded for a communication protocol from the RF front end 705 or I/O controller 772 to information usable by the processor 718. The communication mechanism 770 can include one or more communication components, including wireless wide area network (WWAN) transceiver 774 to communicate with a radio access network (RAN) 776 of a cellular LTE network 778 or an ad hoc mesh network 779. The RAN 776 is generally represented as including a base station, depicted as an evolved base node ("eNodeB") 780 controlled by a radio network controller (RNC) 782 that transmits and receives over a base station antenna 784.

Alternatively, or in addition to a WWAN transceiver 774, communication mechanism 770 can include a wireless local area network (WLAN) module 785 to communicate with wireless devices and network accessible via a wireless access point 786. As an example, the WLAN module 785 may support IEEE 702.11 standards to detect wireless access point 786 as a WiFi hotspot. Alternatively or in addition, the communication mechanism 770 can include a wireless personal area network (WPAN) transceiver 787 for communication with WPAN devices, depicted as a Bluetooth® headset 788 whose use would be indicative of hands-free use. Alternatively or in addition, the communication mechanism 770 can include a near field communication (NFC) transceiver module 789, such as can be utilized for exchanging files with another user device or a payment kiosk 790. As further illustrated, mobile device 704 can also include components for wired communication over the I/O controller 772, such as modem 791 for communicating over a plain old telephone system (POTS) 792 and wired local area network (LAN) interface 793 such as an Ethernet module for connecting to a local area network (LAN) 794. The I/O controller 772 can also serve to connect to wired peripheral devices 795. A global navigation satellite system (GNSS) receiver 796 of the communication mechanism 770 can receive signals from GNSS satellites 797 via the RF front end 705 in order to provide location data. Global Positioning System (GPS) is one example of a GNSS.

Figure 8:
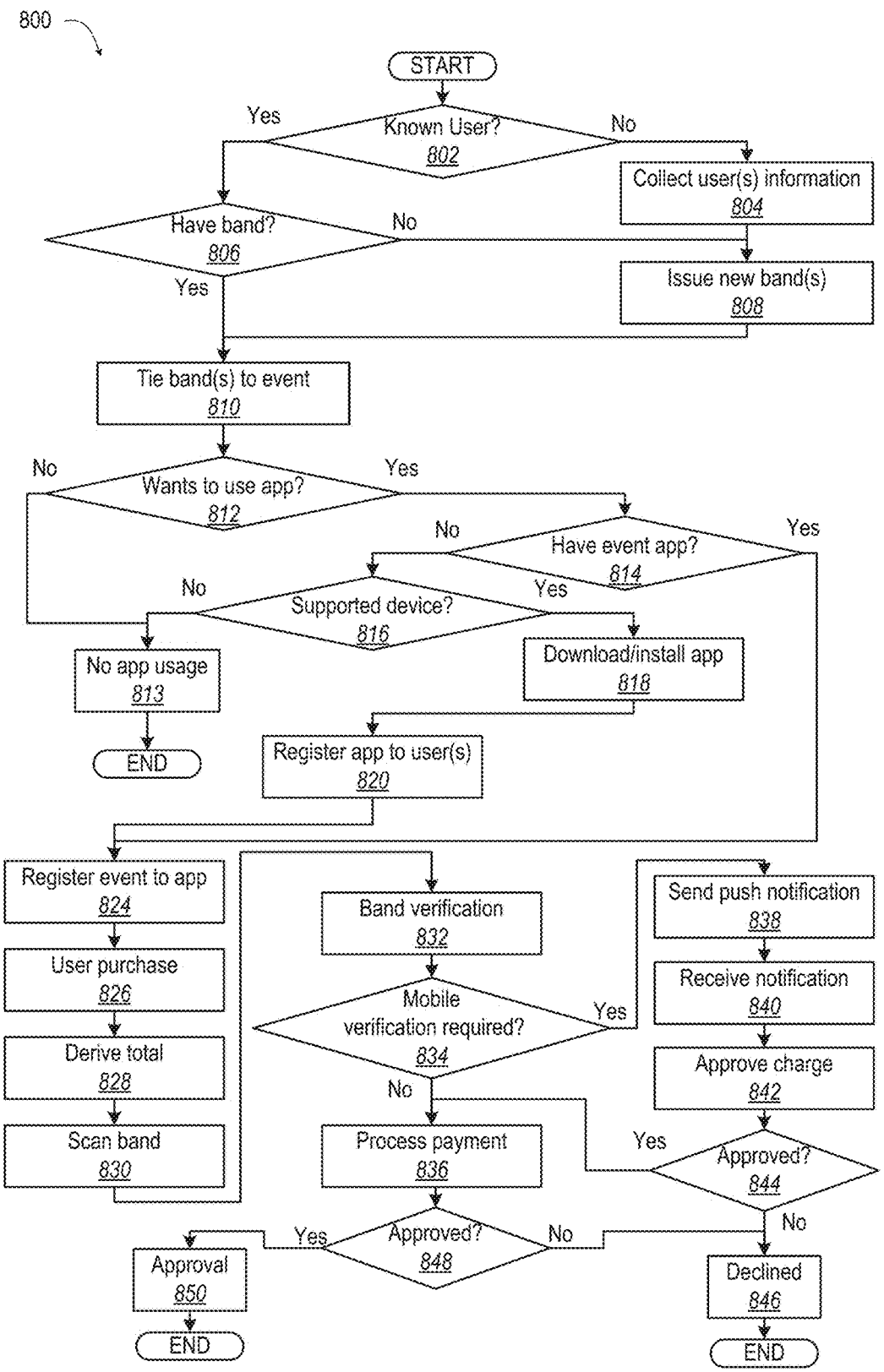
FIG. 8 illustrates method for authenticating users with an identification device for transactions, according to one or more embodiments.

FIG. 8 illustrates a method 800 for authenticating users with an identification device for transactions. In one or more embodiments, the method 800 includes a determination of whether a detected individual is a known user (decision block 802). In response to determining that the detected individual is not a known user in decision block 802, then user information is collected (block 804). In response to determining that the detected individual is a known user in decision block 802, then a further determination is made as to whether the identified user has a band (block 806). In response to determining that the identified individual does not have a band in decision block 806 or after collecting user information in block 804, then a new band is issued (block 808). In response to determining that the identified individual does have a band in decision block 806 or after issuing a new band in block 808, then the band is tied to an event (block 810).

Method 800 includes a determination of whether the identified and associated user wants to use an app that facilitates purchases at an event (decision block 812). In response to determining that the identified and associated user does not want to use the app that facilitates purchases at the event in decision block 812, then no application usage is enabled (block 813). Then method 800 ends. In response to determining that the identified and associated user wants to use the app that facilitates purchases at the event in decision block 812, then the method 800 includes a further determination of whether the user has a mobile device with the event app (decision block 814). In response to a determination that the mobile device does not have the event app in decision block 814, then a further determination is made as to whether the mobile device is a supported device (decision block 816). In response to determining that the mobile device is not a supported device in decision block 816, then the method returns processing to block 813. In response to determining that the mobile device is a supported device in decision block 816, then the app is downloaded and installed on the mobile device (block 818). The new app is registered to the user (block 820).

In response to a determination that the mobile device has the event app in decision block 814 or after registering the downloaded app in block 820, then method 800 includes registering the event to the app (block 824). Method 800 includes user making a purchase (block 826). Merchant derives total of purchase (block 828). Merchant scan band at payment terminal (block 830). Transaction server verifies band (block 832). Transaction server makes a determination whether mobile device verification is required (decision block 834). In response to the transaction server determining that mobile device verification is not required in decision block 834, method includes payment processor processing the payment (block 836). In response to the transaction server determining that mobile device verification is required in decision block 834, method 800 includes transaction server sending push notification to mobile application (block 838). Method 800 includes mobile application receiving notification (block 840). Method 800 includes mobile application receiving user approval of charge (block 842). Method 800 includes mobile application making a determination of whether the user has approved the charge (decision block 844). In response to determining that the user has approved the charge in decision block 844, then method 800 return to block 836 to process the payment. In response to determining that the user has not approved the charge in decision block 844, then method 800 indicates to the merchant that the transaction is declined (block 846). Then method 800 ends. After processing payment in block 836, then method 800 includes a determination of whether the payment processor has approved the payment (decision block 848). In response to determining that the payment processor has approved the payment in decision block 846, then method 800 includes indicating to the merchant that the purchase is approved (block 850). Then method 800 ends. In response to determining that the payment processor has not approved the payment in decision block 846, then method 800 returns to block 846 indicating to the merchant that the purchase is declined (block 846). Then method 800 ends.

In an example embodiment, the UV can be associated with autonomous technology, robotics, predictive analytics, autonomous operation, semi-autonomous operation, machine learning, and machine-to-machine communications.

As stated, the UV system 200 may have wireless communication capabilities enabled using at least the communication circuit. The communication circuit may be communicatively coupled to the processor and configured to communicate with one or more external devices via a network wirelessly of by wires using one or more of the following: a Bluetooth module, a WiFi module, the communication port 206, including a universal serial bus (USB) port, a parallel port, an infrared transceiver port, a radiofrequency transceiver port, and so forth. The mobile robot drone system 200 may have internet connectivity using cellular networks (e.g., 3G, 4G) as well as Wi-Fi and other types of networks. Some additional examples of such networks are GSM, CDMA, LTE, IMS, Universal Mobile Telecommunication System (UMTS), RFID, 4G, 5G, 6G and upper.

A system and method in accordance with the present teachings can provide improved situational awareness by displaying a shared 3D perceptual space and simplifying remote vehicle operation using a supervisory control metaphor for many common remote vehicle tasks. Thus, an operator can task the remote vehicle on a high level using semi-autonomous and/or autonomous behaviors that allow the operator to function as a supervisor rather than having to teleoperate the vehicle. Integration of shared situational awareness can be facilitated by a 3D local perceptual space and point-and-click command and control for navigation and manipulation including target distance estimations. Local perceptual space gives a remote vehicle a sense of its surroundings. It can be defined as an egocentric coordinate system encompassing a predetermined distance (e.g., a few meters in radius) centered on the remote vehicle, and is useful for keeping track of the remote vehicle's motion over short space-time intervals, integrating sensor readings, and identifying obstacles to be avoided. A point-and-click interface can be used by an operator to send commands to a remote vehicle, and can provide a shared, graphical view of the tasking and 3D local environment surrounding the remote vehicle.

A system in accordance with the present teachings can comprise a sensory/computational module and an OCU and customized software applications. The sensory/computational module can include an integrated suite of a global positioning system (GPS), an inertial measurement unit (IMU), video, and range sensors that provide a detailed and accurate 3D picture of the environment around the remote vehicle, which can enable the use of sophisticated autonomous and/or semi-autonomous behaviors and reduce the need for real-time, "high-bandwidth" and highly taxing operator micromanagement (e.g., teleoperation) of the remote vehicle. The autonomous and/or semi-autonomous behaviors can include special routines for, for example: navigation (e.g., click-to-drive); manipulation (e.g., click-to-grip); obstacle detection and obstacle avoidance (ODOA); resolved end-effector motion (e.g., fly-the-gripper); retrotraverse; and self-righting in the event that the remote vehicle has rolled over and can physically provide the actuation necessary for self righting. The OCU includes an application to manage control and feedback of the payload and integrate the payload with a platform (e.g., an iRobot SUGV 310), which allows the OCU to talk to, direct, and manage the payload, and then the payload can command the remote vehicle based on commands received from the OCU. In accordance with certain embodiments, all commands from the OCU are related to the remote vehicle via the payload.

In situations where the remote vehicle is out of sight, map-based localization and a shared 3D local perceptual space can provide the operator with real-time feedback regarding the remote vehicle's position, environment, tasking, and overall status.

Certain embodiments of the present teachings provide: (1) a software architecture that supports a collection of advanced, concurrently-operating behaviors, multiple remote vehicle platforms, and a variety of sensor types; (2) deployable sensors that provide sufficient information to support the necessary level of shared situational awareness between the remote vehicle operator and the on-board remote vehicle autonomy features; (3) lightweight, low-power, high-performance computation that closes local loops using sensors; and (4) a human interface that provides both enhanced situational awareness and transparent tasking of remote vehicle behaviors. Closing local loops refers to the fact that computations and data analyses can be done locally (in the payload) based on sensor feedback, and the payload can then send the results of the computation and/or analysis to the remote vehicle as a command. The payload can also monitor the remote vehicle's progress to ensure the remote vehicle completed the tasks in the command, so that the operator does not have to monitor the remote vehicle's progress.

Certain embodiments of a system in accordance with the present teachings can also comprise a digital radio link built into the OCU configuration and the payload to simplify integration and performance.

The examples presented herein are intended to illustrate potential and specific implementations of the present disclosure. It can be appreciated that the examples are intended primarily for purposes of illustration of the invention for those skilled in the art. No particular aspect or aspects of the examples are necessarily intended to limit the scope of the present invention. For example, no particular aspect or aspects of the examples of system architectures, user interface layouts, or screen displays described herein are necessarily intended to limit the scope of the invention.

It is to be understood that the figures and descriptions of the present invention have been simplified to illustrate elements that are relevant for a clear understanding of the present invention, while eliminating, for purposes of clarity, other elements. Those of ordinary skill in the art will recognize, however, that these sorts of focused discussions would not facilitate a better understanding of the present invention, and therefore, a more detailed description of such elements is not provided herein.

Any element expressed herein as a means for performing a specified function is intended to encompass any way of performing that function including, for example, a combination of elements that performs that function. Furthermore the invention, as may be defined by such means-plus-function claims, resides in the fact that the functionalities provided by the various recited means are combined and brought together in a manner as defined by the appended claims. Therefore, any means that can provide such functionalities may be considered equivalents to the means shown herein.

In various embodiments, modules or software can be used to practice certain aspects of the invention. For example, software-as-a-service (SaaS) models or application service provider (ASP) models may be employed as software application delivery models to communicate software applications to clients or other users. Such software applications can be downloaded through an Internet connection, for example, and operated either independently (e.g., downloaded to a laptop or desktop computer system) or through a third-party service provider (e.g., accessed through a third-party web site). In addition, cloud-computing techniques may be employed in connection with various embodiments of the invention.

Moreover, the processes associated with the present embodiments may be executed by programmable equipment, such as computers. Software or other sets of instructions that may be employed to cause programmable equipment to execute the processes may be stored in any storage device, such as, for example, a computer system (non-volatile) memory, an optical disk, magnetic tape, or magnetic disk. Furthermore, some of the processes may be programmed when the computer system is manufactured or via a computer-readable memory medium.

It can also be appreciated that certain process aspects described herein may be performed using instructions stored on a computer-readable memory medium or media that direct a computer or computer system to perform process steps. A computer-readable medium may include, for example, memory devices such as diskettes, compact discs of both read-only and read/write varieties, optical disk drives, and hard disk drives. A computer-readable medium may also include memory storage that may be physical, virtual, permanent, temporary, semi-permanent and/or semi-temporary.

A "computer," "computer system," "host," "engine," or "processor" may be, for example and without limitation, a processor, microcomputer, minicomputer, server, mainframe, laptop, personal data assistant (PDA), wireless e-mail device, cellular phone, pager, processor, fax machine, scanner, or any other programmable device configured to transmit and/or receive data over a network. Computer systems and computer-based devices disclosed herein may include memory for storing certain software applications used in obtaining, processing, and communicating information. It can be appreciated that such memory may be internal or external with respect to operation of the disclosed embodiments. The memory may also include any means for storing software, including a hard disk, an optical disk, floppy disk, ROM (read only memory), RAM (random access memory), PROM (programmable ROM), EEPROM (electrically erasable PROM) and/or other computer-readable memory media.

In various embodiments of the present invention, a single component may be replaced by multiple components, and multiple components may be replaced by a single component, to perform a given function or functions. Except where such substitution would not be operative to practice embodiments of the present invention, such substitution is within the scope of the present invention. Any of the servers described herein, for example, may be replaced by a "server farm" or other grouping of networked servers (e.g., a group of server blades) that are located and configured for cooperative functions. It can be appreciated that a server farm may serve to distribute workload between/among individual components of the farm and may expedite computing processes by harnessing the collective and cooperative power of multiple servers. Such server farms may employ load-balancing software that accomplishes tasks such as, for example, tracking demand for processing power from different machines, prioritizing and scheduling tasks based on network demand, and/or providing backup contingency in the event of component failure or reduction in operability.

What is claimed is:
1. A system, comprising:
a network architecture comprising:
    a computer system comprising a processor and memory; and
    one or more servers comprising a database communicatively coupled to the computer system; and
at least one user interface;
at least one tracking device configured to transmit location data signals corresponding to the location of the at least one tracking device wherein the at least one tracking device is associated with a robotic agent that is responsive to human interpretable commands; and
an integrated user interface configured to reflect certain content onto the at least one user interface when the tracking device is within a defined operating environment;
wherein the network architecture communicatively couples the at least one tracking device to the at least one user interface and the one or more servers;
wherein the network architecture is configured to
    identify the at least one tracking device and receive location data signals regarding the tracking device within a defined operating environment;
    deliver location data regarding the at least one tracking device to one or more servers;
    determine the location of the tracking device;
    identify the data associated with the robotic agent; and
    delivering content specifically tailored to the robotic agent onto the at least user interface.

2. A method of determining a physical location of a tracking device within an environment, comprising:
providing at least one tracking device configured to transmit location data signals corresponding to the location of the at least one tracking device wherein the at least one tracking device is associated with a robotic agent that is responsive to human interpretable commands;
configuring a network architecture with a computer system to identify each of the tracking devices and receive location data signals regarding each of the tracking devices within a defined operating environment when they are in close proximity to one another, wherein the computer system is communicatively coupled to a database;
receiving the location data signals from the at least one tracking device wherein the network architecture delivers location data regarding the at least one tracking device to one or more servers;
determining, by the computer system, the location of the at least one tracking device and identifying the data associated with the robotic agent; and
configuring the network architecture to enable the one or more servers to project content specifically tailored to the robotic agent to at least one user interface, wherein the content is rendered by the one or more tracking device, a user's mobile device or on one or more computing devices communicatively coupled to the mobile device or the at least one tracking device via one or more networks; wherein an integrated user interface is configured to reflect certain content onto the at least one presentation screen when the mobile device is within a predetermined proximity of the operating environment.

3. A method of authenticating an individual in a transient population, the method comprising:
an unmanned vehicle:
receiving one of a geospatial and a relative location command from a remote control center;
moving to the location associated with the location command;
detecting at least one tracking device configured to transmit location data signals corresponding to the location of the at least one tracking device wherein the at least one tracking device is associated with a robotic agent that is responsive to human interpretable commands; and
a network server in communication with the unmanned vehicle:
configuring a network architecture with a computer system to identify each of the tracking devices and receive location data signals regarding each of the tracking devices within a defined operating environment when they are in close proximity to one another, wherein the computer system is communicatively coupled to a database;
receiving the location data signals from the at least one tracking device wherein the network architecture delivers location data regarding the at least one tracking device to one or more servers;
determining, by the computer system, the location of the at least one tracking device and identifying the data associated with the user; and
configuring the network architecture to enable the one or more servers to project content specifically tailored to the user onto at least one user interface, wherein the content is rendered by the one or more tracking device, a user's mobile device or on one or more computing devices communicatively coupled to the mobile device or the at least one tracking device via one or more networks;
wherein an integrated user interface is configured to reflect certain content onto the at least one user interface when the mobile device is within a predetermined proximity of the operating environment; and
wherein the unmanned vehicle is remotely controlled or autonomous.

* * * * *